United States Patent [19]

Vlock

[11] Patent Number: 4,863,017
[45] Date of Patent: Sep. 5, 1989

[54] AMALGAM CAPSULE

[76] Inventor: David G. Vlock, 12 Fifth Ave., New York, N.Y. 10011-8857

[21] Appl. No.: 269,258

[22] Filed: Nov. 9, 1988

[51] Int. Cl.[4] .................... B65D 25/04; B65D 25/08
[52] U.S. Cl. .................................... 206/219; 366/602
[58] Field of Search ............... 366/602; 206/219, 220, 206/222

[56] References Cited

U.S. PATENT DOCUMENTS

| | | | |
|---|---|---|---|
| 2,487,236 | 11/1949 | Greenberg | 206/220 |
| 3,451,540 | 6/1969 | Kulischenko | 206/220 |
| 4,182,447 | 1/1980 | Kay | 366/602 X |
| 4,362,242 | 12/1982 | Cheetham | 366/602 X |
| 4,450,958 | 5/1984 | Prasad | 206/219 |
| 4,515,267 | 5/1985 | Welsh | 366/602 X |
| 4,557,376 | 12/1985 | Probst et al. | 366/602 X |
| 4,632,243 | 12/1986 | Muhlbauer | 206/219 |

FOREIGN PATENT DOCUMENTS

| | | | |
|---|---|---|---|
| 519008 | 4/1953 | Belgium | 206/220 |
| 043468 | 1/1982 | European Pat. Off. | 206/219 |

Primary Examiner—William Price
Attorney, Agent, or Firm—Notaro & Michalos

[57] ABSTRACT

A capsule for dental amalgam comprises a reservoir portion which has an open end and which contains the silver or silver alloy powder component of the amalgam and a cap portion which has an open end which is meant for containing the liquid or mercury component of the amalgam. A preferably funnel-shaped partition is fixed to the cap portion for retaining the mercury component therein. An orifice is provided in the base of the funnel-shaped partition. The orifice is of a size to prevent leakage of the mercury when the capsule is exposed to accelerations which are below a threshold value and which are typical for storage and transport of the capsule. When the capsule is exposed to acceleration above this threshold value, for example, when the capsule is placed in an amalgamator for mixing the components with each other, the mercury is forced through the orifice and into the powder component. After the amalgam is prepared, the cap can be removed along with its partition to expose the amalgam which is immediately ready for use.

13 Claims, 1 Drawing Sheet

AMALGAM CAPSULE

FIELD AND BACKGROUND OF THE INVENTION

The present invention relates in general to apparatus for mixing dental amalgams and, in particular, to a new and useful capsule which effectively maintains a separation between a liquid component of the amalgam and a solid component thereof until the two components are mixed together to form the amalgam filling.

Dental amalgam fillings are produced by mixing a liquid component, generally mercury, with a powder component, generally silver or silver alloy powder. The mixed amalgam filling is initially sufficiently fluid so that it can be metered into a tooth to be filled. After a certain period of time, however, the amalgam solidifies, whether it has been utilized or not.

Since the amalgam has only a limited useful life after it has been mixed, capsules have been developed which maintain a separation between the liquid and powder components of the amalgam until the amalgam is to be mixed. The capsules are used in conjunction with an amalgamator which vibrates and/or accelerates the capsule to mix the components with each other.

U.S. Pat. No. 4,450,958 to Prasad discloses a self activated dental capsule which maintains the separation between the liquid component and the powder component by confining the liquid component within a foil container. One portion of the foil container is fixed to the interior of the capsule. The loose powder component of the amalgam is housed within the capsule. By vibrating the capsule, the foil container is ruptured, releasing its liquid component which is then mixed with the powder component to form the amalgam. By holding the container against the interior of the capsule, damage to the container beyond its initial rupturing is avoided. This prevents pieces of the container from becoming admixed with the amalgam.

U.S. Pat. No. 4,632,243 to Muhlbauer discloses a foil package for containing both the liquid and solid components of amalgam. The solid component of the amalgam is in the form of a compressed briquet and the rolls of the foil package are rupturable to release and intermix the liquid and solid components. The foil package is meant for use in conjunction with an outer capsule and a mixing apparatus which vibrates the capsule. Under vibration, the package ruptures, releasing and intermixing its components to form the amalgam. Before the amalgam is utilized, however, the ruptured package must be retrieved from the mixed amalgam.

SUMMARY OF THE INVENTION

The present invention is drawn to an amalgam capsule which maintains a secure separation between the liquid and powder components of the amalgam for storage and handling of the capsule. The capsule of the present invention has an interior space which is divided into compartments by a yielding partition which extends across the interior of the capsule. One compartment contains the liquid component, e.g., mercury, and the other compartment contains the powdered component, e.g., silver or silver alloy powder. The yielding partition is structured so that when the capsule is exposed to accelerations below a threshold value, no mercury will pass through the yielding partition. Normal accelerations that the capsule would experience during transport are all below the threshold value. The capsule is exposed to accelerations above the threshold value when the capsule is placed in an amalgamator which vibrates the capsule.

To this end, the yielding partition is either provided with one or more orifices which are of such a small size that, when the capsule is exposed to accelerations below the threshold value, no mercury passes through the orifice. This is due to the natural surface tension of the mercury and its lack of affinity for most surfaces, in particular, plastic surfaces from which the capsule and partition are advantageously made.

In accordance with another embodiment of the invention, the yielding partition may include tear lines which are ruptured by the inertia of the mercury when the capsule is exposed to accelerations above the threshold value.

Accordingly, an object of the present invention is to provide a capsule for dental amalgam which comprises a capsule member defining a closed interior space and yielding partition means fixed to the capsule member and extending across the space to divide the space into a first compartment for a powder component of the amalgam and a second compartment for a liquid component of the amalgam, the yielding partition means retaining the liquid component in the second compartment when the capsule is exposed to acceleration below a threshold value and allowing the liquid to pass into the first compartment when the capsule is exposed to accelerations above the threshold value.

A further object of the present invention is to provide a capsule for dental amalgam which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive manner in which the preferred embodiments of the invention are illustrated.

DESCRIPTION OF THE PREFERRED EMBODIMENTS

Figure 1:
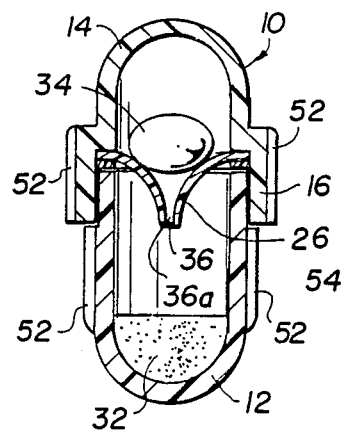
FIG. 1 is an axial sectional view of a capsule for dental amalgam in accordance with the present invention.
Figure 2:
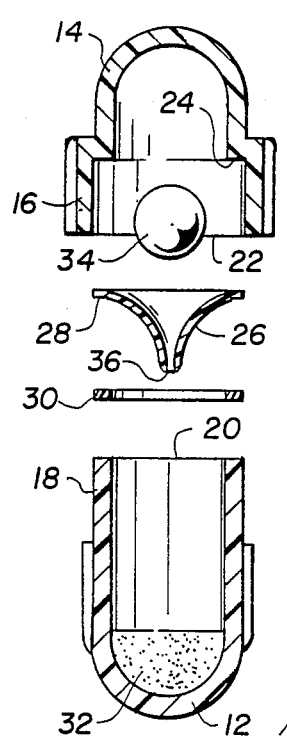
FIG. 2 is an exploded view of the capsule shown in FIG. 1.

Referring to the drawings in particular, the invention embodied in FIGS. 1 and 2 comprises a capsule generally designated 10 for containing the components of dental amalgam. The capsule can be used in conventional mixing apparatus or amalgamators which vibrate the capsule to mix the components with each other and produce amalgam filling.

As shown in FIGS. 1 and 2, capsule 10 comprises a first capsule portion or reservoir 12 which has a closed end for receiving the powder component 32 of the amalgam and an open end 20. A second capsule portion or cap 14 which has a connecting sleeve 16 can be slid onto the outer surface 18 near the open end 20 of reservoir 12 to hermetically enclose the interior space of the capsule. Cap 14 has an upper closed end and a lower open end 22 and defines an interior space for receiving a ball of mercury 34. Mercury 34 is confined in the space of cap 14 by a funnel-shaped yielding partition 26 which includes a lower orifice 36. Partition 26 is advantageously made of synthetic plastic material for which mercury has little or no affinity. Due to the natural surface tension of mercury, the mercury ball 34 tends to form an oval solid, as shown in FIG. 1 which sits in the upper portions of funnel-shaped partition 26. Under the normal accelerations that capsules are exposed to during transport and storage, there is no tendency for mercury 34 to drip through orifice 36. This is caused both by the tapering shape of partition 26, in a direction toward orifice 36, and also, the relatively small diameter of orifice 36. Orifice 36 is advantageously from 0.001 to 0.1 mm in diameter.

FIG. 1 also illustrates the possibility of utilizing an extremely thin, rupturable membrane 36a of material that spans orifice 36 to block any flow of air between the compartment containing the mercury 34 and the compartment containing the powder component 32. This membrane may be made of the same material as the rest of the funnel. Alternatively, the membrane may be made of lacquer or other easily rupturable material. As will be explained later in the specification, it is also advantageous to minimize the air space within the compartment containing the mercury component. This reduces the possible formation of mercury oxides and vapor in the open volume of the compartment.

Figure 3:
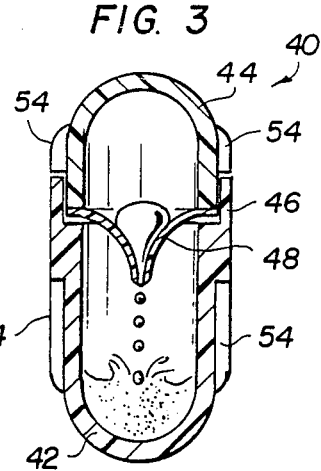
FIG. 3 is a axial sectional view similar to FIG. 1, showing a second embodiment of the invention.

In accordance with the present invention, when capsule 10 is placed in an amalgamator or mixing machine and exposed to accelerations above a threshold value, mercury will be forced down funnel-shaped partition 26 and through orifice 36. This effect is shown in FIG. 3, in connection with the second embodiment of the invention.

The continued vibration of the capsule causes the mercury to mix with the powder and form the amalgam.

After vibration and acceleration of capsule 10, in the amalgamator or mixing machine, cap 14 is removed to expose the now fully mixed amalgam in reservoir 12.

Since the amalgam has only a limited useful life once it has been prepared, it is advantageous to present the amalgam to the dentist in a ready-to-use condition. To this end, funnel-shaped partition 26 has a flange 28 which is fixed against a step 24 in cap 14. This can be done by ultrasonic or other adhesion, or by inclusion of a connecting ring 30 which is slipped into sleeve 16 and fixed against flange 28. In this way, when cap 14 is removed, funnel-shaped partition 26 is also removed, relieving the dentist of having to retrieve any substance or packaging from the amalgam.

Alternatively, partition 26 may simply be seated between the reservoir 12 in cap 14 by the press fit between sleeve 16 and surface 18. With the capsule closed, the yielding partition 26 is thus fixed in position and effectively separates the mercury or liquid component from the dry powder component. This embodiment of the invention does, however, require the additional manipulative step of removing the partition 26 after cap 14 is removed.

FIG. 3 shows a capsule 40 which has a reservoir 42 and a cap 44. Reservoir 42 has an open end with a connecting flange 46 which engages around the surface of cap 44 to form a hermetic press fit seal. Yielding partition 48 is fixed, for example, by welding or adhesive, to the lower edge of cap 44.

In both the embodiments of FIGS. 1 and 3, ridges or knurling 52 and 54 are provided, both on the reservoir and on the cap, to facilitate grasping and twisting of the reservoir and cap for removing the cap from the reservoir.

Although a sliding press fit has been shown in the embodiments of FIGS. 1 through 3 for connecting the reservoir to the cap, the cap may also be threaded to the reservoir with the cap carrying either the internal or the external threads.

Figure 4:
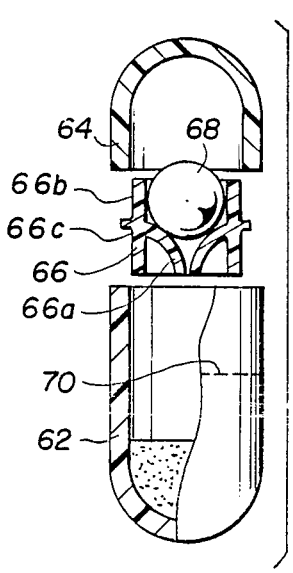
FIG. 4 is an exploded sectional view, partly in elevation of a third embodiment of the invention.

FIG. 4 shows a further embodiment of the invention which includes a reservoir 62 for containing the powder component of the amalgam and a cap 64 for enclosing the liquid or mercury component of the amalgam. In the embodiment of FIG. 4, a separate connecting sleeve 66 is provided which incorporates the yielding partition shown at 66a. Sleeve 66 has an upper outer surface 66b which is slid into the interior of cap 64 and a lower outer surface 66c which is slid into the open end of reservoir 62. In one form of the invention, surface 66b is welded to the interior surface of cap 64 after mercury 68 has been placed in the cap. This forms a one piece cap structure which, when removed from reservoir 62, retains the partition 66a.

In an alternate form of the invention, both surfaces 66b and 66c are welded, advantageously using ultrasonic welding to surfaces of the respective cap 64 and reservoir 62. This produces a hermetically closed and sealed capsule. After the capsule has been vibrated to mix the liquid component with the powder component, the capsule is opened by cutting the capsule along and an indicating mark 70 to expose the now mixed amalgam.

Figure 5:
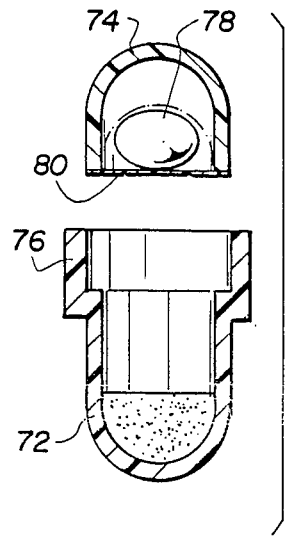
FIG. 5 is an exploded axial sectional view of a fourth embodiment of the invention.

FIG. 5 shows a still further embodiment of the invention, wherein a cap 74 can be hermetically press fit into a connecting sleeve 76 of a reservoir 72 for containing the dry powder component of the amalgam. Cap 74 contains the ball of mercury or liquid component 78, which is retained in the cap by a yielding partition 80 which is in the form of a disk that is adhesively connected or welded to the lower rim of cap 74.

In the embodiment of FIG. 5, it is particularly advantageous to construct cap 74 so as to have an interior volume which is only slightly greater than the volume of the liquid component 78. To this end, cap 74 might either be made smaller than shown in FIG. 5, or the partition 80 may be sealed to the interior of cap 74 at a position closer to the upper end of the cap.

Another possibility is to increase the wall thickness of cap 74 so that with an outer dimension, as shown, the interior volume of the cap is reduced.

As shown in FIGS. 6 through 9, tear lines can be provided in partition 80 which are in the form of a membrane or foil. Tear lines may be triangular, as shown at 82 in FIG. 6, circular, as shown at 84 in FIG. 7, or in the form of a star as shown at 86 in FIG. 8. Any other pattern for tear lines may also be utilized as long as all parts of the membrane remain together and connected to the cap 74. It is essential that no pieces of the membrane fall into the mixed amalgam in the reservoir 72.

As with the size of orifice 36 in the funnel-shaped partition 26, tear lines 82, 84 or 86, are selected so that they rupture when the capsule is exposed to an acceleration above the normal threshold value.

Figure 6:
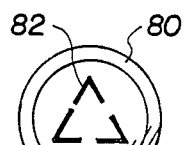
FIG. 6 is a plan view of a yielding partition with tear lines that can be used for the embodiment of FIG. 5.
Figure 7:
FIG. 7 is a view similar to FIG. 6 of a further yielding partition which can be used for the embodiment of FIG. 5.
Figure 8:
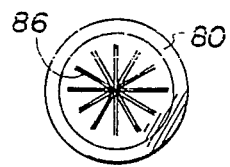
FIG. 8 is a view similar to FIG. 6 of a still further yielding partition which can be used for the embodiment of FIG. 5.

Although tear lines are shown in the embodiments of FIGS. 6 through 8, these lines may be replaced by lines of perforations which either extend completely through the partition or are in the form of point weaknesses which leave a thin, rupturable membrane of material.

Figure 9:
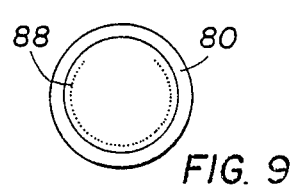
FIG. 9 is a view similar to FIG. 6 of a yielding partition having a peripheral ring of perforations or weakenings for use in the embodiment of FIG. 5.

Referring to FIG. 9, partition 80 includes a peripheral ring of perforations or weakened points which extend most or all of the way around the partition. In the version shown, the peripheral ring of perforations or weakening points 88 extend approximately three quarters of the way around partition 80.

For the purpose of this application, the term "foil" is meant to include membranes or diaphragms made of plastic, ceramic, metal or any other material that has the appropriate strength and, where needed, the appropriate tear characteristics.

While specific embodiments of the invention have been shown and described in detail to illustrate the application of the principles of the invention, it will be understood that the invention may be embodied otherwise without departing from such principles.

What is claimed is:

1. A capsule for dental amalgam comprising:
a capsule member defining a closed interior space; and yielding partition means fixed to said capsule member and extending across said space to divide said space into a first compartment for a powder component of the amalgam and a second compartment for a liquid component of the amalgam, said yielding partition means being structured to retain the liquid component in the second compartment when the capsule is exposed to acceleration below a threshold value and for allowing the liquid component to pass to the first compartment when the capsule is exposed to acceleration above the threshold value; said yielding partition means comprising a partition having an orifice therethrough of a size to prevent passage of liquid component from said second compartment to said first compartment when the capsule is exposed to acceleration below said threshold value and permitting passage of the liquid component through the orifice when the capsule is exposed to acceleration above said threshold value.

2. A capsule for dental amalgam comprising:
a capsule member defining a closed interior space; and yielding partition means fixed to said capsule member and extending across said space to divide said space into a first compartment for a powder component of the amalgam and a second compartment for a liquid component of the amalgam, said yielding partition means being structured to retain the liquid component in the second compartment when the capsule is exposed to acceleration below a threshold value and for allowing the liquid component to pass to the first compartment when the capsule is exposed to acceleration above the threshold value; said yielding partition means comprising a rupturable partition which ruptures when the capsule is exposed to acceleration above said threshold value for releasing the liquid component from said second compartment into said first compartment, with at least one tear line in said partition for facilitating rupturing of said partition.

3. A capsule for dental amalgam comprising:
a capsule member defining a closed interior space; and yielding partition means fixed to said capsule member and extending across said space to divide said space into a first compartment for a powder component of the amalgam and a second compartment for a liquid component of the amalgam, said yielding partition means being structured to retain the liquid component in the second compartment when the capsule is exposed to acceleration below a threshold value and for allowing the liquid component to pass to the first compartment when the capsule is exposed to acceleration above the threshold value; said capsule member comprising a first capsule portion having a closed end and an open end defining said first compartment for containing the powder component of the amalgam, a second capsule portion having a closed end and an open end and defining said second compartment for containing the liquid component of the amalgam, and connector means for detachable connecting said first capsule portion to said second capsule portion with said open ends adjacent to each other for permitting communication between said first and second compartments; said yielding partition means comprising a partition having an orifice therethrough of a size to prevent passage of liquid component from said second compartment to said first compartment when the capsule is exposed to acceleration below said threshold value and permitting passage of the liquid component through the orifice when the capsule is exposed to acceleration above said threshold value.

4. A capsule for dental amalgam comprising:
a capsule member defining a closed interior space; and yielding partition means fixed to said capsule member and extending across said space to divide said space into a first compartment for a powder component of the amalgam and a second compartment for a liquid component of the amalgam, said yielding partition means being structured to retain the liquid component in the second compartment when the capsule is exposed to acceleration below a threshold value and for allowing the liquid component to pass to the first compartment when the capsule is exposed to acceleration above the threshold value; said capsule member comprising a first capsule portion having a closed end and an open end and defining said first compartment for containing the powder component of the amalgam, a second capsule portion having a closed end and an open end and defining said second compartment for containing the liquid component of the amalgam, and connector means for detachably connecting said first capsule portion to said second capsule portion with said open ends adjacent to each other for permitting communication between said first and second compartments; said connector means comprising a connector sleeve which is separate from said first and second capsule portions, said connector sleeve having said yielding partition means fixed thereto; said yielding partition means comprising a partition having an orifice therethrough of a size to prevent passage of liquid component from said second compartment to said first compartment when the capsule is exposed to acceleration below said threshold value and permitting passage of the liquid component through the orifice when the capsule is exposed to acceleration above said threshold value.

5. A capsule according to claim 3, wherein said yielding partition means comprises a yielding partition fixed to said second capsule portion for removal from said first capsule portion when said second capsule portion is detached from said first capsule portion.

6. A capsule according to claim 1, wherein said partition is funnel-shaped and tapers inwardly toward said orifice.

7. A capsule according to claim 3, wherein said connector means comprises a sleeve on one of said first and second capsule portions for engaging an outer surface of the other of said first and second capsule portions for a hermetic press fit.

8. A capsule according to claim 4, wherein said connector sleeve is fixed to said second capsule portion.

9. A capsule according to claim 4, wherein said connector sleeve is fixed both to said first and second capsule portions for sealing said first and second capsule portions to each other.

10. A capsule according to claim 1, wherein said orifice is covered by a rupturable membrane.

11. A capsule according to claim 10, wherein said partition is funnel-shaped and tapers inwardly toward said orifice.

12. A capsule according to claim 2, wherein said tear line comprises a line of perforation which is rupturable.

13. A capsule according to claim 12, wherein said rupturable line comprises a ring extending at least partly around the periphery of said partition.

* * * * *